United States Patent [19]
Wehrmann et al.

[11] Patent Number: 5,874,180
[45] Date of Patent: Feb. 23, 1999

[54] ELECTROLUMINESCENT ARRANGEMENTS AND THEIR USE

[75] Inventors: Rolf Wehrmann, Krefeld; Andreas Elschner, Mülheim; Siegfried Thurm, Meerbusch; Hans Jürgen Rosenkranz, Krefeld; Ralf Dujardin, Willich, all of Germany

[73] Assignee: Bayer AG, Leverkusen, Germany

[21] Appl. No.: 947,835

[22] Filed: Oct. 9, 1997

Related U.S. Application Data

[63] Continuation of Ser. No. 521,107, Aug. 29, 1995, abandoned.

[30] Foreign Application Priority Data

Aug. 30, 1994 [DE] Germany .......................... 44 30 691.1

[51] Int. Cl.$^6$ .................................................. H05B 33/14
[52] U.S. Cl. .......................... 428/690; 428/704; 428/917; 313/504; 558/403; 560/47; 560/50
[58] Field of Search ..................... 428/690, 704, 428/917, 411.1, 457; 313/504; 252/301.16; 558/400, 403; 560/47, 50

[56] References Cited

U.S. PATENT DOCUMENTS

| 4,769,262 | 9/1988 | Ferrar et al. ............................... 428/35 |
| 5,077,142 | 12/1991 | Sakon et al. ............................ 428/690 |

FOREIGN PATENT DOCUMENTS

| 0 406 762 | 1/1991 | European Pat. Off. . |
| 0 557 534 | 9/1993 | European Pat. Off. . |
| 0 595 089 | 5/1994 | European Pat. Off. . |
| 5-179238 | 7/1993 | Japan . |
| WO 92/16023 | 9/1992 | WIPO . |

OTHER PUBLICATIONS

Z.A. Dreger et al., "High pressure effect on the twisted intramolecular charge transfer fluorescence and absorption of p–N,N–dimethylamino–benzylidenemalononitrile (DMABMN) in polymeric matrices", *Chemical Physics*, vol. 166, pp. 193–206, Oct. 01, 1992.

*Primary Examiner*—Marie Yamnitzky
*Attorney, Agent, or Firm*—Connolly & Hutz

[57] ABSTRACT

The invention relates to electroluminescent arrangements (layers) containing special styrenes and to their use.

4 Claims, No Drawings

ELECTROLUMINESCENT ARRANGEMENTS AND THEIR USE

This application is a continuation of application Ser. No. 08/521,107 filed on Aug. 29, 1995 and now abandoned.

This invention relates to electroluminescent arrangements (layers) containing special styrenes and to their use.

Inorganic semiconductors, such as gallium arsenide, are mainly used today in the development of light-emitting components for electronics or photonics. Dot-like indicating elements can be produced on the basis of substances such as these. Large-area arrangements are not possible.

In addition to semiconductor light-emitting diodes, electroluminescent arrangements based on low molecular weight organic compounds applied by vapor deposition are known (for example from U.S. Pat. No. 4,539,507, U.S. Pat. No. 4,769,262, U.S. Pat. No. 5,077,142, EP-A 406 762). With these materials, it is only possible to produce LEDs (light emitting diodes) of small dimensions. In addition, these electroluminescent arrangements have very short lives.

Poly-(p-phenylenes) and poly-(p-phenylene) vinylenes (PPV) show electroluminescence (cf. for example Adv. Mater. 4 (1992), No. 1; J. Chem. Soc. Chem. Commun. 32 (1992)). It is also known that soluble PPV derivatives can be used for the production of flexible plastic LEDs (cf. for example WO 92/16023).

It has now been found that certain substituted styrenes show electroluminescent properties when introduced into corresponding arrangements.

The present invention relates to electroluminescent arrangements, characterized in that styrenes corresponding to formula (I):

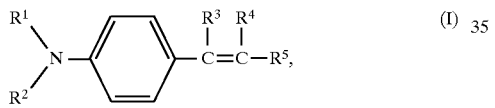

in which $R^1$ and $R^2$ independently of one another represent $C_{1-20}$ alkyl, $C_{6-14}$ aryl, $C_{7-15}$ alkylaryl and $C_{7-15}$ aryl-alkyl, $R^3$ is hydrogen, $C_{1-20}$ alkyl, $C_{6-14}$ aryl, $C_{7-15}$ alkyl-aryl, $C_{7-15}$ arylalkyl, halogen and —CN, $R^4$ and $R^5$ independently of one another represent —CN, COOH, optionally OH-substituted $C_{1-20}$ carboxylate, are used as the electroluminescent substance.

In formula (I), $R^1$ and $R^2$ are preferably methyl, ethyl, propyl, butyl, pentyl, hexyl, heptyl, 2-ethylhexyl, octyl, decyl, dodecyl, myristyl, cetyl, stearyl, phenyl, benzyl, $R^3$ is preferably hydrogen, methyl, ethyl, propyl, butyl, pentyl, hexyl, heptyl, 2-ethylhexyl, octyl, decyl, dodecyl, myristyl, cetyl, stearyl, phenyl, benzyl, alkylphenyl, fluorine, chlorine, bromine, iodine, nitrile (CN), $R^4$ and $R^5$ are preferably nitrile, COOH, COOMe, COOEt, COOProp, COOBu, COOHexyl, COOEthylhexyl, COOOctyl, COODecyl, COODodecyl, COOCetyl, COOHydroxyethyl, COOHydroxypropyl, COOHydroxypropyl, COOHydroxybutyl, COOHydroxyhexyl, COOHydroxyoctyl, COOHydroxydecyl.

The above-mentioned alkyl derivatives of the substituents $R^1$ to $R^5$ may be linear or branched.

The following are examples of styrenes corresponding to formula (I):

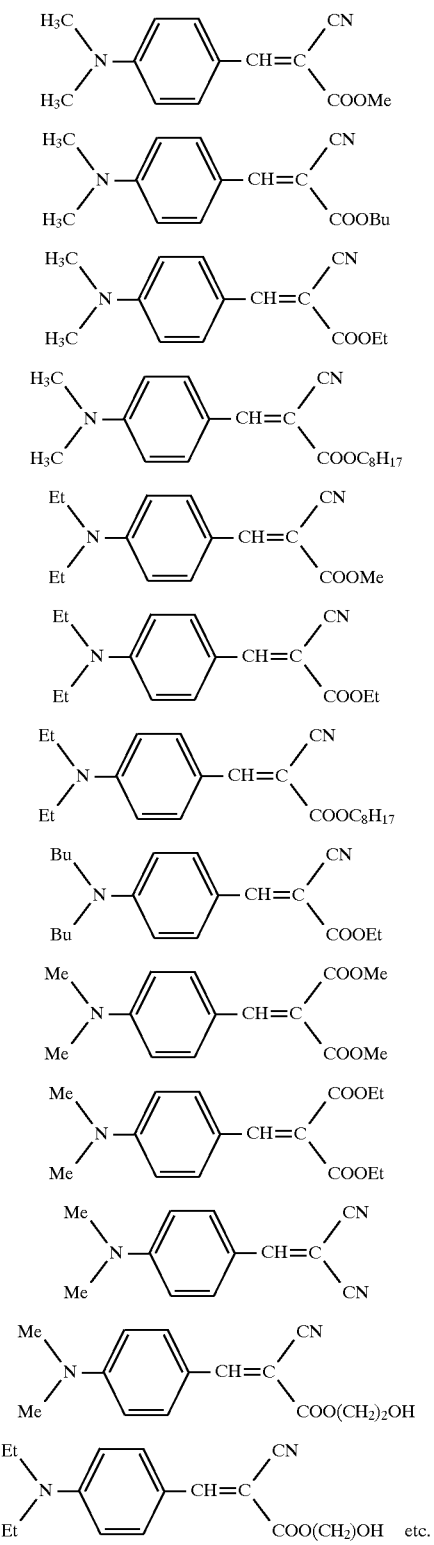

The styrenes of formula (I) to be used in accordance with the invention are known and may be obtained, for example, by the Knoevenagel reaction, i.e. by reaction of, for example, cyanoacetic acid esters (nitrilomalonic acid ester) corresponding to formula (II) with N,N-disubstituted p-aminobenzaldehydes corresponding to formula (III), for example:

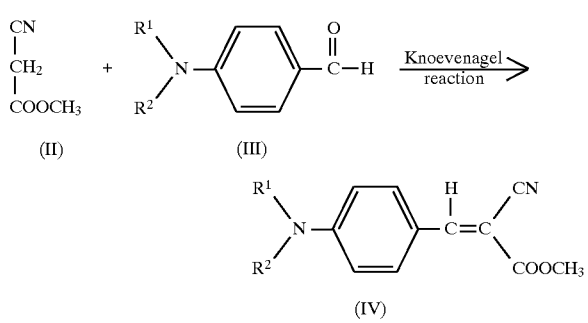

The Knoevenagel reaction, i.e. the reaction of aldehydes and ketones with CH-acidic compounds, is described in detail, for example, in "Organikum", VEB Deutscher Verlag der Wissenschaften, Berlin 1977.

In the systems according to the invention, the electroluminescent (EL) layer is situated between two electrodes. At least one of the two electrodes is transparent in the visible spectral region.

A transparent electrode is applied to a transparent support, for example of glass, plastic (for example PET film). Suitable transparent electrodes (R) are a) metal oxides, for example indium/tin oxide (ITO), tin oxide (NESA), etc.,
b) semitransparent metal films, for example Au, Pt, Ag, Cu, etc.,
c) conductive polymer films, such as polyanilines, polythiophenes, etc.

The metal oxide electrodes and the semitransparent metal film electrodes are applied in thin layers by such techniques as vapor deposition, sputtering, platinizing, etc. The conductive polymer films are applied from solution by such techniques as spin coating, casting, knife-coating, etc.

The thickness of the transparent electrodes is from 50 Å to around several $\mu$m and preferably from 100 Å to 5,000 Å.

The styrenes of formula (I) as the electroluminescent substance are applied to the transparent electrode in the form of a thin film. The thickness of the film is from 30 Å to 10 $\mu$m and preferably from 100 Å to 1 $\mu$m.

After the EL layer has been dried, it is provided with a counterelectrode. The counterelectrode consists of a conductive substance which may be transparent. Suitable counterelectrodes are such metals as Al, Au, Ag, etc. or alloys and oxides thereof which may be applied by such techniques as vapor deposition, sputtering, platinizing.

The arrangement according to the invention is contacted with the two electrodes by two electrical leads (for example metal wires).

The arrangements emit light with a wavelength of 400 to 700 nm when a d.c. voltage of 1 to 100 volts is applied. They show photoluminescence in the range from 400 to 700 nm.

The electroluminescent layer may contain one or more styrenes corresponding to formula (I). In addition, they may optionally contain typical additives, such as inert binders, charge-carrier-transporting substances, mixtures of inert binders and charge-carrier-transporting substances. Charge-carrier-transporting substances increase the intensity of the electroluminescence and reduce the operating voltages.

Preferred inert binders are soluble transparent polymers such as, for example, polycarbonates, polystyrene and copolymers of polystyrene, such as SAN, polysulfones, polyacrylates, polyvinyl carbazole, vinyl acetate and vinyl alcohol polymers and copolymers, etc.

In addition, one or more interlayers may be arranged between the electroluminescent systems and the electrodes. These interlayers—charge-carrier-transporting substances—are known (for example from Appl. Phys. Lett. 57 (1990) 531) where they are referred to as HTLs (hole transport layers) and ETLs (electron transport layers). These interlayers increase the intensity of the electroluminescence.

The arrangements according to the invention may be used for the production of luminescent displays, even in large formats.

EXAMPLES a) Production of an OH-substituted cyanoacetic ester by reaction of a cyanoacetic acid ester with ethylene glycol

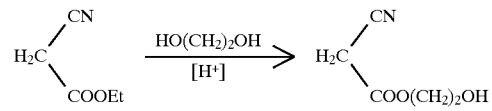

4 Moles of cyanoacetic acid ethyl ester are heated to the reflux temperature with 4 moles of ethylene glycol and 3 g of p-toluene sulfonic acid. Ethanol is eliminated and is removed through a column. The residue is distilled in a high vacuum. The product is characterized from its NMR spectrum.

b) Production of a long-chain cyanoacetic acid ester by reaction of cyanoacetic acid methyl ester with 2-ethyl hexanol

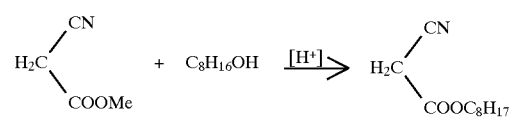

4 Moles of cyanoacetic acid methyl ester are heated under reflux with 4.4 moles of 2-ethyl hexanol and 3 g of p-toluene sulfonic acid until the theoretical quantity of methanol has been eliminated and removed by distillation. The residue is fractionated in a water jet vacuum.

The butyl, hexyl and benzyl esters are similarly obtained.

c) Reaction of cyanoacetic acid esters with N,N-dialkylaminobenzaldehydes to form 2,4-(N,N-dimethylamino-phenyl)-cyanoacrylic acid hydroxyethyl ester (Knoevenagel reaction)

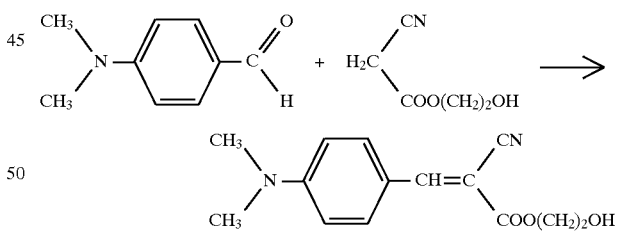

0.75 Mole of dimethylaminobenzaldehyde and 0.75 mole of the cyanoacetic acid ester from a) are refluxed in 200 ml of toluene on a water separator with addition of 1.5 g of piperidine and 1.2 g of glacial acetic acid until the theoretical quantity of water has been eliminated.

The product precipitated after cooling is washed with water and then with petroleum ether and recrystalized from toluene. $^1$H-NMR (ppm): 8.12 CH=; 4.22 and 3.69 OCH$_2$; CH$_3$N.

The cyanoacetic esters from Example b) are similarly reacted.

d) Electroluminescent arrangement I ITO-coated glass (manufactured by Balzers) is cut into 20×30 mm pieces and cleaned in the following steps:

1. 15 mins. in dist. water/Falterol rinse (basic) in an ultrasonication bath,
2. rinse for 2×15 mins. in fresh dist. water in the ultrasonication bath,
3. 15 mins. in ethanol in the ultrasonication bath,
4. 2×15 mins. in fresh acetone in the ultrasonication bath,
5. dry on fluff-free lens cloths.

0.45 Part by weight of poly-(9-vinylcarbazole) (Aldrich Chemical Co., Ltd. #18, 260-5) and 1.05 part by weight of the electroluminescent styrene corresponding to formula (I) with $R^1=CH_3$, $R^2=CH_3$, $R^3=H$, $R^4=CN$, $R^5=$COOEthylhexyl are dissolved in dichloroethane. The solution is filtered (0.2 μm filter). Using a paint thrower, the filtered solution is spread over the ITO glass at 1,000 r.p.m. The thickness of the dry film is 230 nm and the Ra value of the surface is 10 nm (Alpha-Step 200 stylus profilometer of Tencor Inst.).

Al electrodes are then applied to the film thus produced by vapor deposition. To this end, isolated Al dots 3 mm in diameter are deposited onto the film using a hole mask. A pressure p of <10-5 mbar prevails in the apparatus used for vapor deposition.

The ITO layer and the Al electrode are connected to a voltage source by electrical leads. When the voltage is increased, an electrical current flows through the arrangement and the described layer electroluminescent. The electroluminescence occurs irrespective of the polarity of the voltage applied.

The luminance of the electroluminescence is 100 cd/m² at 25 volts (Minolta, LS 100).

e) Electroluminescent arrangement II

In accordance with the production of the electroluminescent arrangement I, the electroluminescent layer was produced from a dichloroethane solution containing 0.7 part by weight of polystyrene and 0.3 part by weight of a styrene corresponding to formula (I) with $R^1=CH_3$, $R^2=CH_3$, $R^3=H$, $R^4=CN$ and $R^5=CN$.

The luminance of the electroluminescence is 5 cd/m² at 40 volts.

f) Further electroluminescent arrangements

In accordance with the production of electroluminescent arrangements I and II, electroluminescent layers were produced from 0.3 part by weight of polymeric binders and 0.7 part by weight of a styrene corresponding to formula I with $R_1=CH_3$, $R_2=CH_3$, $R_3=H$, $R_4=CN$ and $R_5=COOCH_3$. The layers were approximately 150 nm thick. Polyvinyl carbazole (PVC), styrene/acrylonitrile (SAN), polymethyl methacrylate (PMMA), polystyrene (PS) and polycarbonate (PC) were used as polymeric binders.

All the arrangements show electroluminescence beyond an applied voltage of around 15 volts.

We claim:

1. An electroluminescent device comprising an electroluminescent layer between a pair of electrodes, wherein the electroluminescent layer comprises a styrene corresponding to formula (I):

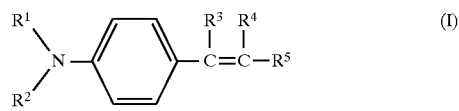

in which $R^1$ and $R^2$ independently of one another are $C_{1-20}$ alkyl, $C_{6-14}$ aryl, $C_7$ alkylaryl or $C_7$ arylalkyl $R^3$ is ethyl, propyl, butyl, pentyl, hexyl, 2-ethylhexyl, octyl, decyl, dodecyl, myristyl, cetyl, stearyl, phenyl, benzyl, alkylphenyl, fluorine, chlorine, bromine, iodine or —CN, $R^4$ is —CN, and $R^5$ is —CN.

2. An electroluminescent device comprising an electroluminescent-layer between a pair of electrodes, wherein the electroluminescent layer comprises a styrene corresponding to formula (I):

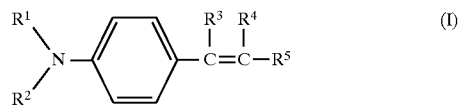

in which $R^1$ and $R^2$ independently of one another are $C_{1-20}$ alkyl, $C_{6-14}$ aryl, $C_{7-15}$ alkylaryl or $C_7$ arylalkyl, $R^3$ is hydrogen, $C_{1-20}$ alkyl, $C_{6-14}$ aryl, $C_{7-15}$ alkylaryl, $C_7$ arylalkyl, halogen or —CN, and $R^4$ and $R^5$ independently of one another are COOH, $C_{1-20}$ carboxylate, or OH-substituted $C_{1-20}$ carboxylate.

3. An electroluminescent device according to claim 2, wherein $R^5$ is COOEthylhexyl, COOOctyl, COODecyl, COODodecyl, COOCetyl or OH-substituted $C_{1-20}$ carboxylate.

4. An electroluminescent device according to claim 2, wherein $R^4$ and $R^5$ independently of one another are COOEthylhexyl, COOOctyl, COODecyl, COODodecyl, COOCetyl or OH-substituted $C_{1-20}$ carboxylate.

* * * * *

UNITED STATES PATENT AND TRADEMARK OFFICE
CERTIFICATE OF CORRECTION

PATENT NO. : 5,874,180

DATED : February 23, 1999

INVENTOR(S) : Wehrmann et al.

It is certified that error appears in the above-identified patent and that said Letters Patent is hereby corrected as shown below:

In Column 6, line 16 (claim 1), "$C_7$ alkylaryl or $C_7$ arylalkyl" should read --$C_{7-15}$ alkylaryl or $C_{7-15}$ arylalkyl--.

In Column 6, line 24 (claim 2), "electroluminescent-layer" should read --electroluminescent layer--.

In Column 6, line 35 (claim 2), "$C_7$ arylalkyl" should read --$C_{7-15}$ arylalkyl--.

In Column 6, line 37 (claim 2), "$C_7$ arylalkyl" should read --$C_{7-15}$ arylalkyl--.

Signed and Sealed this

Tenth Day of April, 2001

Attest:

NICHOLAS P. GODICI

*Attesting Officer*     *Acting Director of the United States Patent and Trademark Office*